US00PP33908P3

(12) United States Plant Patent
Schoone

(10) Patent No.: US PP33,908 P3
(45) Date of Patent: Jan. 25, 2022

(54) ***PHALAENOPSIS* PLANT NAMED 'FIERY FLAMES'**

(50) Latin Name: *Phalaenopsis hybrida*
Varietal Denomination: Fiery Flames

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/339,973

(22) Filed: Jun. 5, 2021

(65) Prior Publication Data

US 2021/0385997 P1 Dec. 9, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

*Primary Examiner* — June Hwu
(74) *Attorney, Agent, or Firm* — C. Anne Whealy

(57) ABSTRACT

A new and distinct cultivar of *Phalaenopsis* plant named 'Fiery Flames', characterized by its relatively upright plant habit; moderately vigorous growth habit; strong flowering stems; strong and relatively small leaves; freely flowering habit with typically two inflorescences per plant, each inflorescence with numerous flowers; yellow to yellow green-colored flowers proximally blushed with greyed orange; and good postproduction longevity.

2 Drawing Sheets

Figure 1:
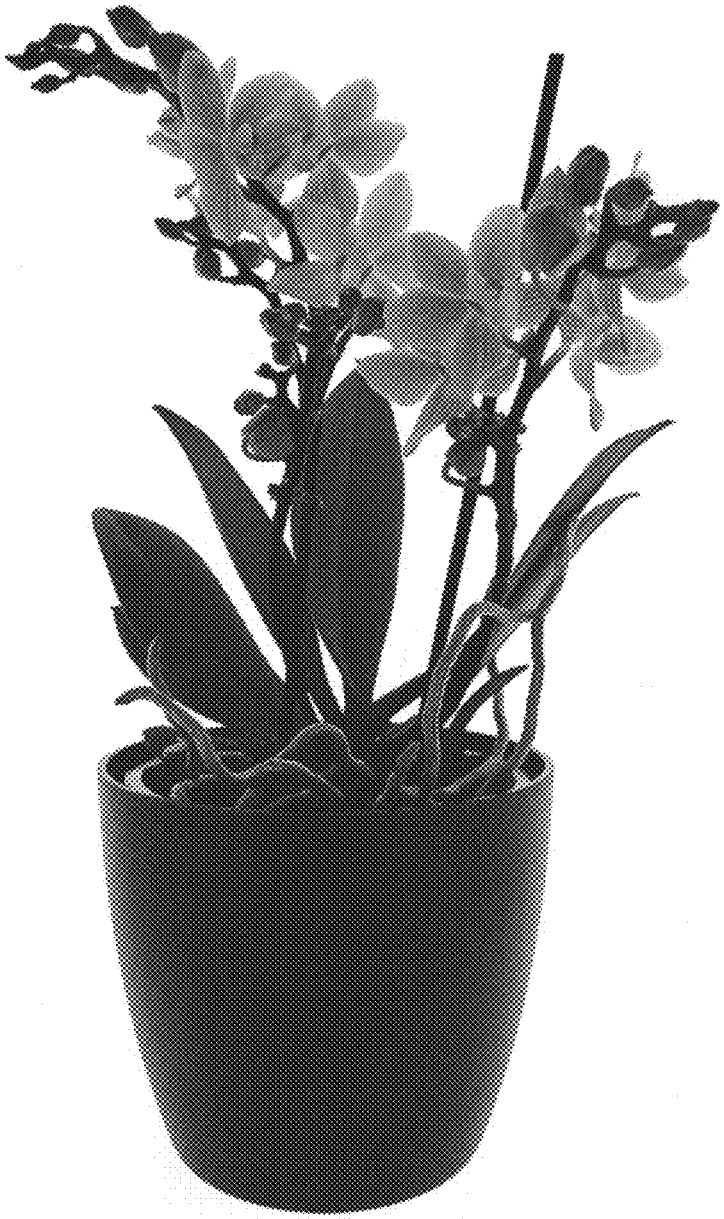

Botanical designation: *Phalaenopsis hybrida.*
Cultivar denomination: 'FIERY FLAMES'.

CROSS-REFERENCED TO CLOSELY-RELATED APPLICATIONS

Title: Varieties of *Phalaenopsis* Plants
Inventor: René Schoone
Filed: Jun. 6, 2020
Ser. No. 62/705,003
Inventor and Applicant/Assignee hereby claims the benefit of this provisional U.S. Patent Application.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Floricultura B.V. of Heemskerk, The Netherlands on Mar. 18, 2021, application number 2021/0830. Foreign priority is not claimed to this European Community Plant Breeder's Rights application. The new *Phalaenopsis* had an original denomination of 'Firefly', however, this denomination was rejected by the European Community Plant Variety Office and the denomination was subsequently changed to 'Fiery Flames'. In the provisional U.S. Plant patent application Ser. No. 62/705,003, this variety is referred by the original denomination, 'Firefly'.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Fiery Flames'.

The new *Phalaenopsis* plant is a product of a planned breeding program conducted by the Inventor in Nantou, Taiwan and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in February, 2013 in Nantou, Taiwan of *Phalaenopsis hybrida* 'Jiuhbao Sweetie', not patented, as the female, or seed, parent with *Phalaenopsis hybrida* 'Pingtung Fire Rose', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in February, 2018.

Asexual reproduction of the new *Phalaenopsis* plant by in vitro meristem propagation in a controlled environment in Assendelft, The Netherlands since February, 2019 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Fiery Flames'. These characteristics in combination distinguish 'Fiery Flames' as a new and distinct *Phalaenopsis* plant:

1. Relatively upright plant habit.
2. Moderately vigorous growth habit.
3. Strong flowering stems.
4. Strong and relatively small leaves.
5. Freely flowering habit with typically two inflorescences per plant, each inflorescence with numerous flowers.
6. Yellow to yellow green-colored flowers proximally blushed with greyed orange.
7. Good postproduction longevity.

Plants of the new *Phalaenopsis* can be compared to plants of the female parent, 'Jiuhbao Sweetie'. Plants of the new *Phalaenopsis* differ primarily from plants of 'Jiuhbao Sweetie' in flower color as plants of the new *Phalaenopsis* have yellow to yellow green-colored flowers proximally blushed with greyed orange whereas plants of 'Jiuhbao Sweetie' have purple red-colored flowers. In addition, flower labella of plants of the new *Phalaenopsis* do not have cirrose tips whereas flower labella of plants of 'Jiuhbao Sweetie' have cirrose tips.

Plants of the new *Phalaenopsis* can be compared to plants of the male parent, 'Pingtung Fire Rose'. Plants of the new *Phalaenopsis* differ primarily from plants of 'Pingtung Fire Rose' in flower color as plants of the new *Phalaenopsis* have yellow to yellow green-colored flowers proximally blushed with greyed orange whereas plants of 'Pingtung Fire Rose' have purple red-colored flowers. In addition, the curvature of the labellum is weaker in plants of the new *Phalaenopsis* than plants of 'Pingtung Fire Rose'.

Plants of the new *Phalaenopsis* can be compared to plants of *Phalaenopsis hybrida* 'Goldrush', not patented. In side-by-side comparisons, plants of the new *Phalaenopsis* differ primarily from plants of 'Goldrush' in flower shape as flower labella of plants of the new *Phalaenopsis* do not have cirrose tips whereas flower labella of plants of 'Goldrush' have cirrose tipes. In addition, the curvature of the labellum is weaker in plants of the new *Phalaenopsis* than plants of 'Goldrush'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Fiery Flames' grown in a container.

Figure 2:
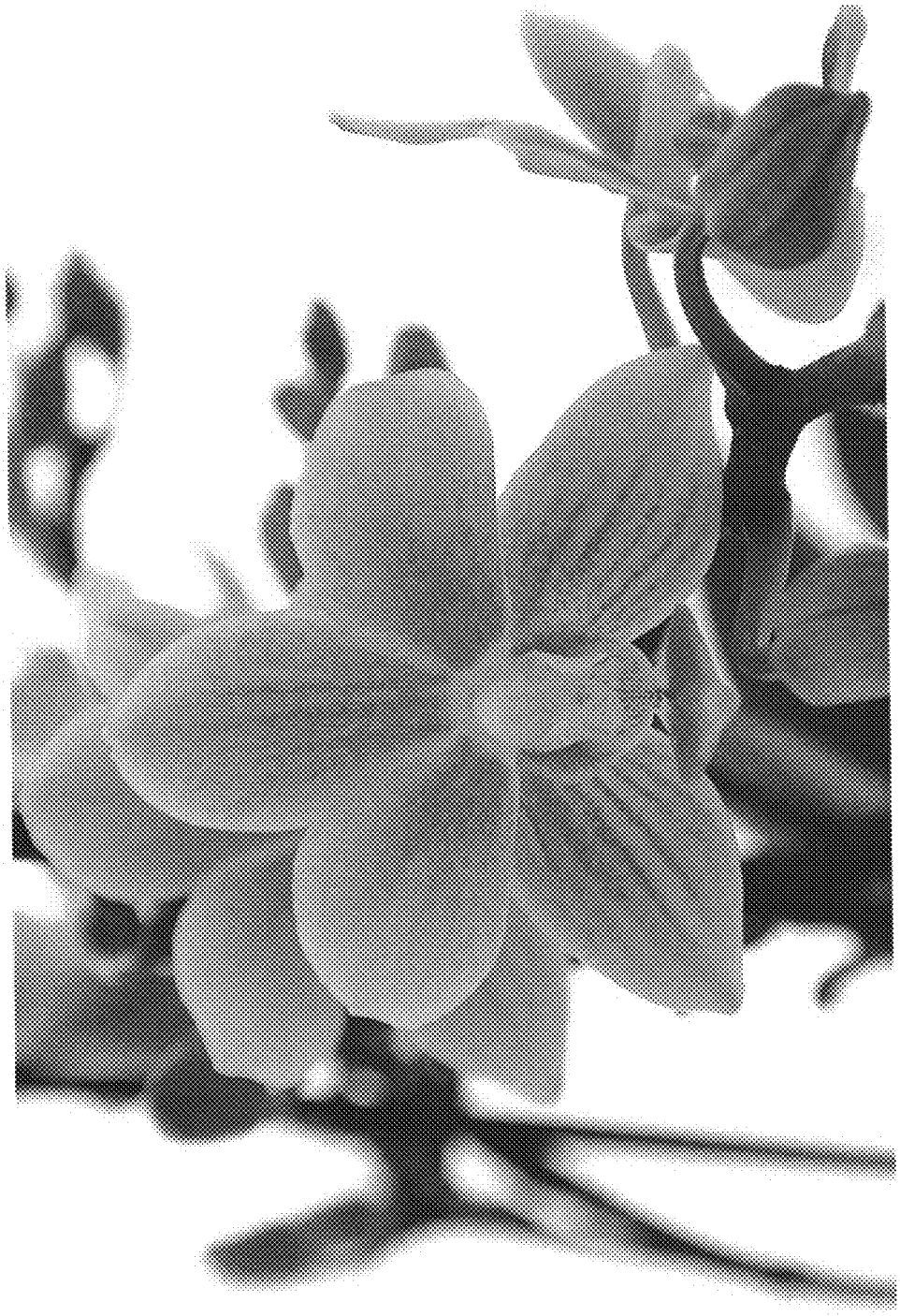

The photograph on the second sheet (FIG. 2) is a close-up view of a typical flower of 'Fiery Flames'.

DETAILED BOTANICAL DESCRIPTION

The aforementioned photographs and following observations and measurements describe plants grown during the early spring in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Fiery Flames'.

Parentage:

*Female parent.*—*Phalaenopsis hybrida* 'Jiuhbao Sweetie', not patented.

*Male parent.*—*Phalaenopsis hybrida* 'Pingtung Fire Rose', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically grey to green in color; actual color of the roots is dependent on substrate composition, water quality, fertilizer, substrate temperature and age of roots.

*Rooting habit.*—Low amount of branching; medium density.

Plant description:

*Plant form and growth habit.*—Herbaceous epiphyte; relatively compact and upright plant habit with typically two inflorescences per plant, each inflorescence with numerous flowers; monopodial; moderately vigorous and moderate to slow growth rate.

*Plant height, substrate level to top of foliar plane.*—About 13.3 cm.

*Plant height, substrate level to top of inflorescences.*—About 20 cm.

*Plant diameter or spread.*—About 19.9 cm.

Leaf description:

*Arrangement and quantity.*—Distichous, simple; sessile; about seven leaves per plant.

*Length.*—About 12.3 cm.

*Width.*—About 4.4 cm.

*Aspect.*—Upright to outwardly arching.

*Shape.*—Oblanceolate to narrowly elliptic to oblanceolate; slightly carinate.

*Apex.*—Unequal narrowly acute.

*Base*.—Sheathing. Sheath length: About 1.6 cm. Sheath width: About 8 mm. Sheath color: Close to 143C tinged with close to 164A.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to a blend of 137B and 146A. Developing leaves, lower surface: Close to 146A to 146B; towards the margins and main vein, tinged with close to 197A. Fully expanded leaves, upper surface: Close to a blend of 137A and 146A; venation, close to 146A. Fully expanded leaves, lower surface: Close to 146C; towards the margins, tinged with close to N199A; venation, close to N199A and N199B.

Inflorescence description:

*Appearance and flowering habit*.—Showy zygomorphic flowers arranged on axillary branched racemes; typically two inflorescences per plant; each inflorescence with about 20 flowers; flowers face outwardly on arching inflorescences supported by upright peduncles; flowers with three petals, two lateral petals and one center petal transformed into a lateral petals and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 16.2 cm.

*Inflorescence width*.—About 8.1 cm.

*Flower buds*.—Height: About 1.3 cm. Diameter: About 8 mm by 10 mm. Shape: Broadly ovate. Color: Upper surface, close to a blend of 144A and 144B; under surface, close to a blend of 144B and 144C and tinged with close to 177B.

*Flower size*.—About 4.2 cm (vertical) by 4.1 cm (horizontal).

*Flower depth*.—About 2.3 cm.

*Petals, quantity and arrangement*.—Three, two lateral petals and one center petal transformed into a labellum. Length: About 2.1 cm. Width: About 1.6 cm. Shape: Obovate to broadly elliptic. Apex: Broadly and bluntly acute to mucronulate. Margin: Entire. Texture and luster, upper and lower surfaces: Smooth, glabrous, velvety; matte. Color: When opening, upper surface: Close to 151B; towards the base, close to 166C. When opening, lower surface: Close to a blend of N144D and 151C; towards the margins, slightly tinged with close to 166D and at the margin edges, close to 151C to 151D; main vein, close to 166C. Fully opened, upper surface: Close to a blend of 11A and 153D, proximally blushed with close to 164A; towards the apex, close to 151B; color does not change with subsequent development. Fully opened, lower surface: Close to 151C to 151D; towards the margins, close to 153D; main vein, close to 166C to 166D; color does not change with subsequent development.

*Labella*.—Appearance: Three-parted with two lateral lobes and a central lobe; development of cirrose tips has not been observed. Length, lateral lobes: About 1 cm. Width, lateral lobes: About 4 mm. Length, central lobe: About 2.1 cm. Width, central lobe: About 2 mm to 10 mm. Shape, lateral lobes: Oblong. Shape, central lobe: Narrowly rhomboidal. Apex, lateral lobes: Obtuse. Apex, central lobe: Shallowly emarginate. Margins, lateral lobes: Entire; slightly convex. Margins, central lobe: Finely dentate. Texture and luster, upper and lower surfaces: Smooth, glabrous, moderately velvety; matte. Callosities: Located at the base of the labellum and attachment point of the labellum; about 3 mm in length, about 2 mm in width and about 2 mm in height. Color: When opening, upper surface: Lateral lobes: Close to 157C; distally, close to 186D with stripes, close to 59C and 59D; at the base, dots, close to N167C and 172B. Central lobe: Close to 180A; towards the apex, close to N155C and at the apex, close to 149C; basal margin, close to 162A to 162D; towards the base, close to 157D and at the base (at column connection), close to 17B with fine dots, close to 174B to 174C. Callosities: Close to 158B; fine dots, close to 174B to 174C. When opening, lower surface: Lateral lobes: Close to 157C; distally, close to 186C. Central lobe: Close to N170B; center along main vein, close to 195C; distally, close to 149C to 149D; towards the base, close to 157D and at the base (at column connection), close to 14C. Fully opened, upper surface: Lateral lobes: Close to 155B; distally, close to 186D with stripes, close to 59C and 59D; at the base, dots, close to N167C and 172B. Central lobe: Close to 180A; towards the apex, close to N155C and at the apex, close to 149C; basal margin, close to 162A to 162D; towards the base, close to 157D and at the base (at column connection), close to 17B with fine dots, close to 174B to 174C. Callosities: Close to 158C; fine dots, close to 174C. Fully opened, lower surface: Lateral lobes: Close to 157C; distally, close to 186B to 186C. Central lobe: Close to 182D to lighter than 182D; center along main vein, close to 195D; distally, close to 149D; towards the base, close to 157D and at the base (at column connection), close to 14D.

*Sepals*.—Quantity and arrangement: Three, one upper dorsal sepal and two lower lateral sepals. Length, dorsal sepal: About 2.3 cm. Width, dorsal sepal: About 1.3 cm. Length, lateral sepals: About 2.2 cm. Width, lateral sepals: About 1.5 cm. Shape, dorsal sepal: Elliptic to slightly obovate. Shape, lateral sepals: Ovate. Apex, dorsal sepal: Minutely emarginate. Apex, lateral sepals: Bluntly acute. Base, dorsal and lateral sepals: Truncate. Margin, dorsal sepal: Entire. Margin, lateral sepals: Entire; coarsely undulate. Texture and luster, dorsal and lateral sepals, upper and lower surfaces: Smooth, glabrous, velvety; matte. Color, dorsal sepal: When opening, upper surface: Close to a blend of 150B and 151C; proximally, blushed with close to 166C. When opening, lower surface: Close to a blend of 151A and 152D; venation, close to 152B. Fully opened, upper surface: Close to a blend of 151C and 153D; proximally, blushed with close to 166C to 166D. Fully opened, lower surface: Close to 151A; towards the margins, close to 151C; proximally, blushed with close to 166D. Color, lateral sepals: When opening, upper surface: Close to 145A to 145B tinged with close to 151C; along veins, fine dots, close to 166C. When opening, lower surface: Close to 151A; venation, close to 152B. Fully opened, upper surface: Close to 151C and 151D; along veins, fine dots, close to 166C and 166D. Fully opened, lower surface: Close to 151A; towards the margins, close to 151C; main vein, close to 177C and lateral venation, close to 166D.

*Peduncles*.—Length: About 22.9 cm. Diameter: About 3.5 mm. Strength: Strong. Aspect: Upright to outwardly arching. Texture and luster: Smooth, glabrous; matte. Color: Close to 200A; sparsely to moderately covered with fine dots, close to 146A to 146B.

*Pedicels*.—Length: About 1.9 cm. Diameter: About 2 mm. Strength: Moderately strong. Aspect: About 55° from peduncle axis. Texture and luster: Smooth, glabrous; matte. Color: Close to 145B and 145C; proximally, close to 146B and 148A.

*Reproductive organs*.—Androecium: Column length: About 9 mm. Column width: About 4 mm. Column color: Close to NN155D; at the apex, close to NN155A. Pollinia quantity: Two. Pollinia diameter (per two pollinia): About 2 mm. Pollinia color: Close to 17B. Gynoecium: Stigma length: About 3 mm. Stigma width: About 3.5 mm. Stigma shape: Reniform. Stigma color: Close to N155A. Ovary length: About 5 mm. Ovary diameter: About 0.75 mm. Ovary color: Close to 145B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Fiery Flames' as illustrated and described.

* * * * *